US008322191B2

(12) United States Patent
Fritz

(10) Patent No.: US 8,322,191 B2
(45) Date of Patent: Dec. 4, 2012

(54) ENHANCED CAVITY FOR A PHOTOACOUSTIC GAS SENSOR

(75) Inventor: Bernard Fritz, Eagan, MN (US)

(73) Assignee: Honeywell International Inc., Morristown, NJ (US)

( * ) Notice: Subject to any disclaimer, the term of this patent is extended or adjusted under 35 U.S.C. 154(b) by 160 days.

(21) Appl. No.: 12/827,873

(22) Filed: Jun. 30, 2010

(65) Prior Publication Data

US 2012/0000271 A1 Jan. 5, 2012

(51) Int. Cl.
*G01N 21/01* (2006.01)
*G01N 23/10* (2006.01)

(52) U.S. Cl. ....................................... 73/24.02; 356/437

(58) Field of Classification Search .................. 356/432, 356/437; 73/24.02

See application file for complete search history.

(56) References Cited

U.S. PATENT DOCUMENTS 4,051,372 A 9/1977 Aine
4,233,568 A 11/1980 Hamerdinger et al.
4,612,647 A 9/1986 Norvell
4,614,961 A 9/1986 Khan et al.
4,672,624 A 6/1987 Ford
4,732,480 A 3/1988 Fortunato et al.
4,795,258 A 1/1989 Martin
4,818,882 A 4/1989 Nexo et al.
4,870,224 A 9/1989 Smith et al.
4,973,131 A 11/1990 Carnes
5,022,745 A 6/1991 Zayhowski et al.
5,040,895 A 8/1991 Laurent et al.
5,135,304 A 8/1992 Miles et al.
5,146,465 A 9/1992 Khan et al.
5,278,435 A 1/1994 Van Hove et al.
5,311,280 A 5/1994 Koper et al.
5,408,319 A 4/1995 Halbout et al.
5,418,868 A 5/1995 Cohen et al.
5,450,053 A 9/1995 Wood
5,468,910 A 11/1995 Knapp et al.
5,512,750 A 4/1996 Yanka et al.
5,528,040 A 6/1996 Lehmann (Continued)

FOREIGN PATENT DOCUMENTS

DE 3311808 10/1984

(Continued)

OTHER PUBLICATIONS

L.-Y. Hao, S. Qiang, G.-R. Wu, L. Qi, D. Feng et al., "Cylindrical mirror multipass Lissajous system for laser photoacoustic spectroscopy," Rev. Sci. Instrum. vol. 73, No. 5, pp. 2079-2085, (2002).*

(Continued)

*Primary Examiner* — Lisa Caputo
*Assistant Examiner* — Punam Roy
(74) *Attorney, Agent, or Firm* — Seager Tufte & Wickhem LLC

(57) ABSTRACT

Photoacoustic cells for gas sensors are described. In some instances, the photoacoustic cell may be configured to provide an increased internal path length of the light beam in the photoacoustic cell relative to, for example, a conventional cylindrical photoacoustic cell. The photoacoustic cell may be shaped to provide increased internal reflection of the light within the photoacoustic cell, thereby increasing the absorption of the light by a gas to be detected in the photoacoustic cell. One example photoacoustic cell that can provide such increased internal reflection may be a generally conical-shaped.

13 Claims, 6 Drawing Sheets

U.S. PATENT DOCUMENTS

| | | | |
|---|---|---|---|
| 5,544,186 | A | 8/1996 | Sauer et al. |
| 5,550,373 | A | 8/1996 | Cole et al. |
| 5,629,951 | A | 5/1997 | Chang-Hasnain et al. |
| 5,677,538 | A | 10/1997 | Moustakas et al. |
| 5,679,965 | A | 10/1997 | Schetzina |
| 5,723,706 | A | 3/1998 | Brasier et al. |
| 5,739,554 | A | 4/1998 | Edmond et al. |
| 5,797,490 | A | 8/1998 | Fujii et al. |
| 5,815,277 | A | 9/1998 | Zare et al. |
| 5,832,017 | A | 11/1998 | Ramdani et al. |
| 5,834,331 | A | 11/1998 | Razeghi |
| 5,835,231 | A | 11/1998 | Pipino |
| 5,847,397 | A | 12/1998 | Moustakas |
| 5,869,896 | A | 2/1999 | Baker et al. |
| 5,900,650 | A | 5/1999 | Nitta |
| 5,909,280 | A | 6/1999 | Zavracky |
| 5,912,740 | A | 6/1999 | Zare et al. |
| 5,915,051 | A | 6/1999 | Damask et al. |
| 5,933,245 | A | 8/1999 | Wood et al. |
| 5,933,565 | A | 8/1999 | Diebold |
| 5,960,025 | A | 9/1999 | Thorland et al. |
| 5,982,788 | A | 11/1999 | Hemmati |
| 6,040,895 | A | 3/2000 | Haas |
| 6,080,988 | A | 6/2000 | Ishizuya et al. |
| 6,084,682 | A | 7/2000 | Zare et al. |
| 6,091,504 | A | 7/2000 | Walker et al. |
| 6,115,122 | A | 9/2000 | Bao et al. |
| 6,122,416 | A | 9/2000 | Ooba et al. |
| 6,147,756 | A | 11/2000 | Zavracky et al. |
| 6,208,798 | B1 | 3/2001 | Morozov et al. |
| 6,233,052 | B1 | 5/2001 | Zare et al. |
| 6,275,296 | B1 | 8/2001 | Numai |
| 6,287,940 | B1 | 9/2001 | Cole et al. |
| 6,295,130 | B1 | 9/2001 | Sun et al. |
| 6,296,799 | B1 | 10/2001 | Sato et al. |
| 6,310,904 | B1 | 10/2001 | Thorland et al. |
| 6,324,192 | B1 | 11/2001 | Tayebati |
| 6,335,669 | B1 | 1/2002 | Miyazaki et al. |
| 6,377,350 | B1 | 4/2002 | Paldus et al. |
| 6,380,531 | B1 | 4/2002 | Sugihwo et al. |
| 6,384,953 | B1 | 5/2002 | Russell et al. |
| 6,393,894 | B1 | 5/2002 | Bonne et al. |
| 6,404,648 | B1 | 6/2002 | Slupe et al. |
| 6,406,578 | B1 | 6/2002 | Schober et al. |
| 6,421,127 | B1 | 7/2002 | McAndrew et al. |
| 6,424,419 | B1 | 7/2002 | Tazartes et al. |
| 6,438,149 | B1 | 8/2002 | Tayebati et al. |
| 6,452,680 | B1 | 9/2002 | Paldus et al. |
| 6,483,130 | B1 | 11/2002 | Yang et al. |
| 6,483,149 | B1 | 11/2002 | Mosher et al. |
| 6,490,034 | B1 | 12/2002 | Woias et al. |
| 6,492,726 | B1 | 12/2002 | Quek et al. |
| 6,507,107 | B2 | 1/2003 | Vaiyapuri |
| 6,535,327 | B1 | 3/2003 | Vodopyanov |
| 6,545,739 | B1 | 4/2003 | Matsumoto et al. |
| 6,583,917 | B2 | 6/2003 | Melloni et al. |
| 6,584,126 | B2 | 6/2003 | Wang et al. |
| 6,590,710 | B2 | 7/2003 | Hara et al. |
| 6,594,059 | B2 | 7/2003 | Flanders |
| 6,597,713 | B2 | 7/2003 | Ouchi |
| 6,608,711 | B2 | 8/2003 | Flanders et al. |
| 6,627,983 | B2 | 9/2003 | Tu et al. |
| 6,658,034 | B2 | 12/2003 | Garnache et al. |
| 6,670,559 | B2 | 12/2003 | Centola et al. |
| 6,670,599 | B2 | 12/2003 | Wagner et al. |
| 6,728,286 | B2 | 4/2004 | Thorland et al. |
| 6,741,381 | B1 | 5/2004 | Levenson et al. |
| 6,784,946 | B1 | 8/2004 | Schroter et al. |
| 6,792,010 | B2 | 9/2004 | Koulikov et al. |
| 6,816,636 | B2 | 11/2004 | Cole et al. |
| 6,836,501 | B2 | 12/2004 | Cox et al. |
| 6,859,284 | B2 | 2/2005 | Rella et al. |
| 6,865,198 | B2 | 3/2005 | Taubman |
| 6,879,014 | B2 | 4/2005 | Wagner et al. |
| 6,959,023 | B1 | 10/2005 | Xie et al. |
| 6,959,024 | B2 | 10/2005 | Paldus et al. |
| 6,967,976 | B2 | 11/2005 | Xie et al. |
| 6,970,484 | B2 | 11/2005 | Paldus et al. |
| 6,985,281 | B2 | 1/2006 | Wagner et al. |
| 7,002,697 | B2 | 2/2006 | Domash et al. |
| 7,012,696 | B2 | 3/2006 | Orr et al. |
| 7,015,457 | B2 | 3/2006 | Cole et al. |
| 7,035,298 | B2 | 4/2006 | Vodopyanov et al. |
| 7,046,362 | B2 | 5/2006 | Lehmann et al. |
| 7,049,004 | B2 | 5/2006 | Domash et al. |
| 7,050,170 | B2 | 5/2006 | Chilese et al. |
| 7,064,836 | B2 | 6/2006 | Bechtel et al. |
| 7,089,781 | B2 | 8/2006 | Petrovic et al. |
| 7,101,431 | B2 | 9/2006 | Miner |
| 7,106,763 | B2 | 9/2006 | Tan et al. |
| 7,113,256 | B2 | 9/2006 | Butler et al. |
| 7,113,286 | B2 | 9/2006 | Yan |
| 7,116,423 | B2 | 10/2006 | Paldus et al. |
| 7,145,165 | B2 | 12/2006 | Cox et al. |
| 7,147,165 | B2 | 12/2006 | Mongin et al. |
| 7,147,695 | B2 | 12/2006 | Mitra |
| 7,154,595 | B2 | 12/2006 | Paldus et al. |
| 7,173,754 | B2 | 2/2007 | Vodopyanov et al. |
| 7,221,827 | B2 | 5/2007 | Domash et al. |
| 7,259,856 | B2 | 8/2007 | Kachanov et al. |
| 7,263,871 | B2 | 9/2007 | Selker et al. |
| 7,265,842 | B2 | 9/2007 | Paldus et al. |
| 7,304,799 | B2 | 12/2007 | Ma et al. |
| 7,352,464 | B2 | 4/2008 | Chen et al. |
| 7,369,242 | B2 | 5/2008 | Cole et al. |
| 7,420,686 | B2 | 9/2008 | Tan |
| 7,535,573 | B2 | 5/2009 | Kachanov et al. |
| 7,586,114 | B2 | 9/2009 | Cole et al. |
| 7,612,885 | B2 | 11/2009 | Cole et al. |
| 7,649,189 | B2 | 1/2010 | Cole |
| 7,656,532 | B2 | 2/2010 | Cole |
| 7,663,756 | B2 | 2/2010 | Cole |
| 2002/0017452 | A1 | 2/2002 | Zimmermann et al. |
| 2002/0191268 | A1 | 12/2002 | Seeser et al. |
| 2004/0234198 | A1 | 11/2004 | Wagner et al. |
| 2004/0255853 | A1 | 12/2004 | Ma et al. |
| 2005/0030628 | A1 | 2/2005 | Wagner et al. |
| 2005/0082480 | A1 | 4/2005 | Wagner et al. |
| 2005/0105184 | A1 | 5/2005 | Ma et al. |
| 2005/0254056 | A1 | 11/2005 | Kachanov et al. |
| 2007/0133001 | A1 | 6/2007 | Cox et al. |
| 2007/0146720 | A1 | 6/2007 | Cox et al. |
| 2007/0195434 | A1 | 8/2007 | Koulikov et al. |
| 2008/0137089 | A1 | 6/2008 | Tan |
| 2009/0113988 | A1 | 5/2009 | Koulikov |
| 2009/0185175 | A1 | 7/2009 | Cole et al. |
| 2009/0323055 | A1 | 12/2009 | Cole et al. |
| 2010/0027012 | A1 | 2/2010 | Fritz et al. |

FOREIGN PATENT DOCUMENTS

| | | |
|---|---|---|
| DE | 19635421 | 12/1997 |
| EP | 0177918 | 3/1991 |
| EP | 0667548 | 8/1995 |
| EP | 1069658 | 1/2001 |
| EP | 1070943 | 1/2001 |
| EP | 1847825 | 10/2007 |
| EP | 1061618 | 11/2007 |
| GB | 2358245 | 7/2001 |
| JP | 03252172 | 11/1991 |
| JP | 05095130 | 4/1993 |
| JP | 7288334 | 10/1995 |
| KR | 1020060087792 | 8/2006 |
| WO | 9326049 | 12/1993 |
| WO | 9942875 | 8/1999 |
| WO | 2004068123 | 8/2004 |
| WO | 2006000120 | 1/2006 |

OTHER PUBLICATIONS

D. Qu, Z. Liu, C. Gmachl, "A compact asymmetric chaotic optical cavity with long optical path lengths," Appl. Phys. Lett. 93, 014101 (2008).*

E. Narimanov, J. Fan, and C. Gmachl, "Compact quasi-chaotic optical cavity," 2005 Quantum Electronics an Laser Science Conference. pp. 421-423.*

D. Qu and C. Gmachl, "Quasichaotic optical multipass cell," Physical Review A 78, 033824 (2008).*

Bernstein et al., "Development of a Miniature Silicon PhotoAcoustic Gas Sensor," Presented at Opto 96, Leipzig, Germany, 6 pages, Sep. 26-29, 1999.
Brown, et al., "Visible-Blind UV Digital Camera Based on a 32*32 Array of GAN/AIGAN P-I-N Photodiodes," MRS Internet Journal of Nitride Semiconductor Research, vol. 4S1, pp. 1-10, Sep. 1999.
Campargue et al., "Measurement of SiH2 Density in a Discharge by Intracavity Laser Absorption Spectroscopy and CW Cavity Ring-Down Spectroscopy," Journal of Physics D. Applied Physics, vol. 31, No. 10 pp. 1168-1175, May 21, 1998.
Chitica et al., "Monolithic InP-Based Tunable Filter with 10-nm Bandwidth for Optical Data Interconnects in the 1550-nm Band," IEEE Photonics Technology Letters, vol. 11, No. 5, pp. 584-586, May 1999.
Chou et al., "Diode-Laser Measurements of He-, Ar-, and N2-Broadened HF Lineshapes in the First Overtone Band," Journal of Molecular Spectroscopy 196, pp. 70-76, 1999.
Chung et al., "Design and Fabrication of 10x10 Micro-Spatial Light Modulator Array for Phase and Amplitude Modulation," Sensors and Actuators, vol. 78, No. 1, pp. 63-70, Jan. 1999.
Cole et al., "Microscopic Spectroscopy of Optical MEMS Devices," Topic 2 (Materials and Technology), Honeywell Laboratories, 2 pages, on or Around Dec. 11, 2000.
U.S. Appl. No. 12/826,095, filed Jun. 29, 2010, Publication Date: Dec. 29, 2011.
Edwards, "Multiple-Traverse Absorption Cell Design," Journal of the Optical Society of America, vol. 51, No. 1, pp. 98-102,Jan. 1961.
Ferber et al., "A Miniature Silicon Photoacoustic Detector for Gas Monitoring Applications", presented at the MTEX International Conference on Sensors and Transducers, Birmingham, UK, 7 pages, Feb. 14, 2001.
Gillis et al., "Photoacoustic Spectroscopy for Quantitation of Trace Gases in Air," 2 pages, Chemical Science and Technology Laboratory National Institute of Standards and Technology, Industrial and Analytical Instruments and Services Forensics and Homeland Security, 2 pages, prior to Jul. 21, 2008.
He et al., "High-Resolution Cavity Ring-Down Absorption Spectroscopy of Nitrous Oxide and Chloroform Using a Near-Infrared CW Diode Laser," Chemical Physics Letters, vol. 289, pp. 527-534, Jun. 19, 1998.
Jerman et al., "A Miniature Fabry-Perot Interferometer with a Corrugated Silicon Diaphragm Support," Sensors and Actuators, vol. A29, No. 2, pp. 151-158, Nov. 1991.
Kurochkin et al., "Complex-Cavity Two-Mode CO2 Laser for Saturated Intracavity Absorption Spectroscopy," Optical Spectroscopy, vol. 68, No. 6, pp. 793-797, 1990.
Kurochkin et al., "Three-Mirror Cavity CO2 Laser for Intracavity Saturated-Absorption Spectroscopy," Optical Spectroscopy, vol. 65, No. 2, pp. 265-267, 1988.
Manfredi et al., "JFET Preamplifiers for Low Noise Applications in Calorimetry and Radiation Spectroscopy," Nuclear Physics B (Proc. Suppl.) 44, pp. 613-616, 1995.
O'Keefe et al., "Cavity Ring-Down Optical Spectrometer for Absorption Measurements Using Pulsed Laser Sources," Review of Scientific Instruments, 59, 11 pages, 1988.
Paul et al., "Cavity Ringdown Measures Trace Concentrations," Laser Focus World, pp. 71-80, Mar. 1997.
Pipino et al., "Evanescent Wave Cavity Ring-Down Spectroscopy with a Total-Internal-Reflection Minicavity," Rev. Sci. Instrum., vol. 68, No. 8, pp. 2978-2989, Aug. 1997.
Raymond et al., "Use of a Monolithic Dual JFET in a Low Cost, Low Noise, Charge-Sensitive Preamplifier for Semiconductor Radiation Detectors," Phys. Med. Biol., vol. 33, No. 3, pp. 367-372, 1988.
Richman et al., "Continuously Tunable, Single-Longitudinal-Mode, Pulsed Mid-Infrared Optical Parametric Oscillator Based on Periodically Poled Lithium Niobate," Optical Society of America, vol. 17, No. 7, pp. 1233-1239, Jul. 2000.
Sadeghi et al., "Cavity Ring Down Spectroscopy Applied to Plasma Diagnostics," Proc. Int. Symp. Laser-aided Plasma Diagnostics Lake Tahoe, CA, 8 pages, Sep. 1999.
Scherer et al., "Infrared Cavity Ringdown Laser Absorption Spectroscopy (IR-CRLAS) in Low Pressure Flames," Applied Physics B., vol. 64, pp. 699-705, 1997.
Schiwon et al., "Terahertz Cavity-Enhanced Attenuated Total Reflection Spectroscopy," Applied Physics Letters, vol. 86, 2005.
Schweber, "An Old Communications Problem Reoccurs in Optical-Communication-System Design—How it Works: Making the Laser Diode Tunable", EDN, 3 pages, Sep. 28, 2000.
Shimizu et al., "Stark Spectroscopy by 10μ Lasers Using a Multipath Cell," Journal of Applied Physics, vol. 46, No. 1, pp. 258-259, Jan. 1975.
Siegman, Lasers, Chapter 11-13, Copyright 1986.
Smirnov et al., "Dye Lasers Using a Three-Mirror Cavity with Lamp Excitation," 4 pages, 1981.
Spence et al., "A Laser-Locked Cavity Ring-Down Spectrometer Employing an Analog Detection Scheme," Review of Scientific Instruments, vol. 71, No. 2, pp. 347-353, Feb. 2000.
Sze, "Physics of Semiconductor Devices." pp. 763-765, John Wiley & Sons, N.Y., 1982.
Tayebati et al., "Microelectromechanical Tunable Filter with Stable Half Symmetric Cavity," Electronics Letters, IEE Stevanage, GB, vol. 34, No. 20, pp. 1967-1968, Oct. 1998.
Tayebati et. al., "Widely Tunable Fabry-Perot Filters Using High Index-Contrast DBRs," Design and Manufacturing of WDM Devices, Dallas, Texas, Nov. 4-5, 1997, SPIE vol., 3234, pp. 206-218, 1998.
Yang et al., "Back-Illuminated GAN/AIGAN Heterojunction Photodiodes With High Quantum Efficiency and Low Noise," Applied Physics Letters, vol. 73, No. 8, pp. 1086-1088, XP000777678, Aug. 24, 1998.
Search Report for Corresponding Application No. 11170750.1-1234/2402735 Dated Dec. 21, 2011.

* cited by examiner

ENHANCED CAVITY FOR A PHOTOACOUSTIC GAS SENSOR

FIELD

The present disclosure relates generally to gas sensors, and more particularly, to photoacoustic gas sensors.

BACKGROUND

Gas sensors are widely used in many diverse applications, including commercial applications, military applications, and private applications. The sensitivity of such gas sensors can vary, and the type of gas sensor used for a particular application is often selected depending on the required sensitivity and cost. For many commercially available photoacoustic gas sensors, the sensitivity may be based, in part, on the length of the internal optical path of the photoacoustic sensor. Increasing the optical path length can impact the sensitivity and operation of such sensors.

SUMMARY

The present disclosure relates generally to gas sensors, and more particularly, to photoacoustic gas sensors. In one illustrative embodiment, a photoacoustic gas sensor is disclosed that increases the internal path length of a light beam in the photoacoustic cell, which may increase the absorption of the light by a gas to be detected in the photoacoustic cell. The photoacoustic gas sensor may include an electromagnetic radiation source configured to emit electromagnetic radiation, a photoacoustic cell configured to receive a gas sample to be detected, and a detector acoustically coupled to the photoacoustic cell. The photoacoustic cell may include an optical element adjacent the photoacoustic cell. In some cases, a rear wall of the optical element may define a first wall of the photoacoustic cell. The optical element may transmit at least part of the electromagnetic radiation into the photoacoustic cell. The photoacoustic cell may be shaped such that the electromagnetic radiation that is transmitted into the photoacoustic cell is reflected off of internal surfaces of the photoacoustic cell at least two times before returning to the rear wall of the optical element. In some cases, the photoacoustic cell may be shaped and/or configured such that the electromagnetic radiation transmitted into the photoacoustic cell is reflected at least one time off the rear wall of the optical element.

The preceding summary is provided to facilitate a general understanding of some of the innovative features unique to the present disclosure and is not intended to be a full description. A full appreciation of the disclosure can be gained by taking the entire specification, claims, drawings, and abstract as a whole.

BRIEF DESCRIPTION

The invention may be more completely understood in consideration of the following detailed description of various illustrative embodiments of the disclosure in connection with the accompanying drawings, in which.

DESCRIPTION

Figure 1:
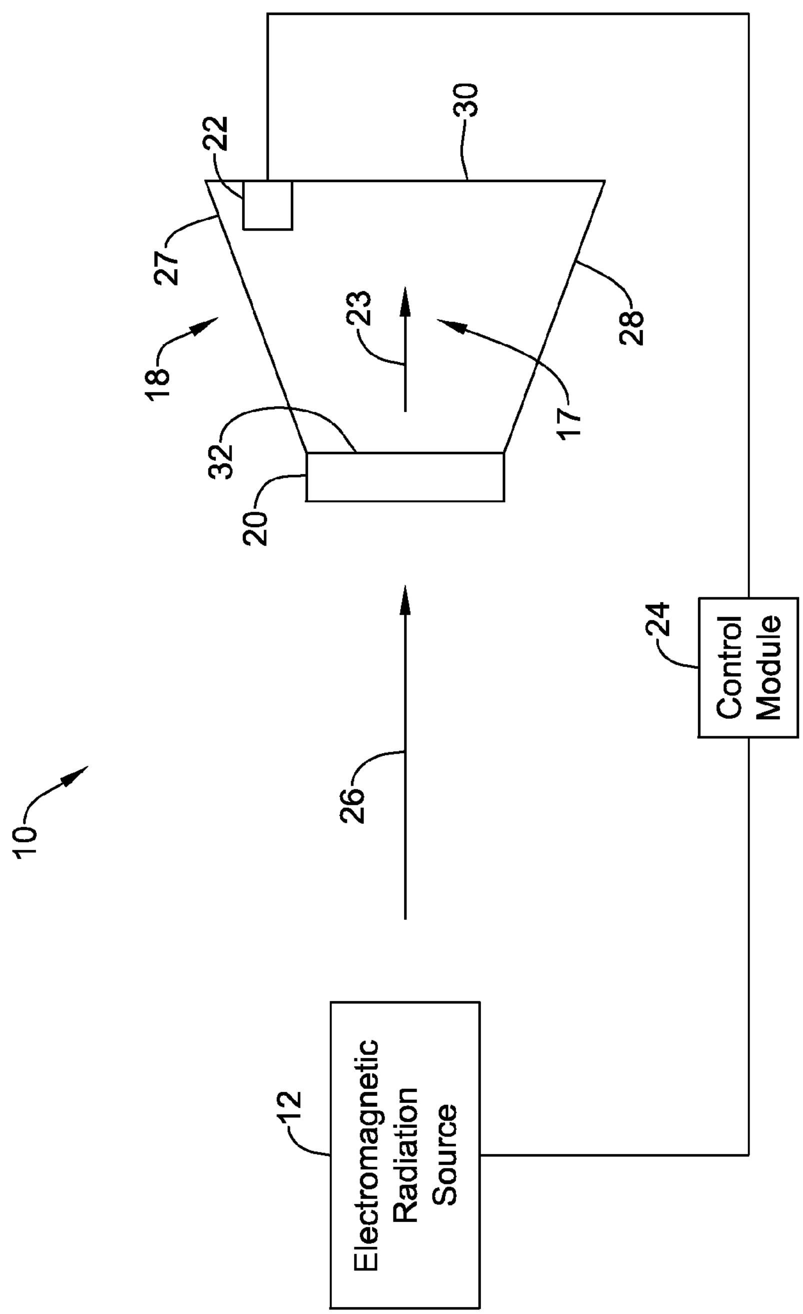
FIG. 1 is a schematic diagram of an illustrative photoacoustic gas detection system.

The following description should be read with reference to the drawings wherein like reference numerals indicate like elements throughout the several views. The detailed description and drawings show several embodiments which are meant to be illustrative of the claimed invention.

FIG. 1 is a schematic diagram of an illustrative photoacoustic gas detection system 10 that may be used to detect a concentration of a gas sample in an environment. In the illustrative embodiment, the photoacoustic gas detection system 10 may include an electromagnetic radiation source 12 configured to emit electromagnetic radiation, such as light beam 26, a photoacoustic cell 18 configured to receive a sample of a gas to be detected, and a detector 22 configured to detect the interaction (e.g. absorption) of the electromagnetic radiation with the gas sample.

In the illustrative embodiment, the electromagnetic radiation source 12, which in some cases may be a laser, a light-emitting diode (LED), a lamp, or any other suitable light source, may be configured to emit electromagnetic radiation, such as light beam 26. In some cases, electromagnetic radiation source 12 may be a collimated light source, such as a laser, or in other cases, may be a non-collimated light source. When a non-collimated light source is provided, the light beam 26 may be focused to a location inside the photoacoustic cell 18 using one or more optical elements such as lenses, but this is not required.

While not required, the electromagnetic radiation source 12 may be tunable to different wavelengths, which may be useful to help identify a particular gas species in the gas sample. When so provided, the light beam 26 may be tuned to an absorption line, or wavelength close thereto, of a gas to be detected. Alternatively, an electromagnetic radiation source 12 having a fixed wavelength (i.e. non-tunable) may be used. In this case, the electromagnetic radiation source 12 may be selected to have a wavelength that is close to or at an absorption line of a gas to be detected. In some cases, multiple electromagnetic radiation sources may be used, each providing a wavelength of light that is tuned to an absorption line of a different gas. It is contemplated that any suitable electromagnetic radiation source 12 may be used.

In the illustrative embodiment, the photoacoustic cell 18 is configured to receive a sample of gas for detection. In some cases, the photoacoustic cell 18 may include a membrane that allows a gas sample to migrate into a cavity 17 of the photoacoustic cell 18. The photoacoustic cell 18 can be defined by one or more walls, such as front wall 32, back wall 30, and side walls 27 and 28, which collectively define a cavity 17 in the illustrative embodiment. In some instances, the photoacoustic cell 18 may be configured to provide an increased internal path length of the internal light beam 23 for a given volume of the cavity 17. In some cases, the photoacoustic cell 18 may be shaped such that at least a majority of the internal light beam 23 is reflected off of the internal walls of the photoacoustic cell 18 at least two times before returning to the back side of the optical element 20. Alternatively, or in addition, the photoacoustic cell 18 may be shaped such that at least a majority of the internal light beam 23 has an incident angle that is greater than a threshold angle at least a first time the internal light beam 23 returns and strikes the back side of the optical element 20. These are just some examples. Increasing the volume of cavity 17 may significantly reduce the photoacoustic signal in the cavity 17, which can significantly reduce the signal-to-noise ratio of the photoacoustic gas detection system 10.

In many cases, the side walls, such as side walls 27 and 28, may be configured such that the cross-sectional area defined by the side walls increases from the front wall 32 toward the back wall 30 (such as in a cone or similar shape, as shown in FIG. 1). In some embodiments, at least one of side walls 27 and 28 may be positioned at a non-orthogonal angle relative to the front wall 32 and/or back wall 30, however, this is not required. As shown in FIG. 1, both side walls 27 and 28 may intersect the front wall 32 an angle greater than 90 degrees, such as, for example, 110 degrees. In this example, side walls 27 and 28 may also intersect the back wall 30 at an angle less than 90 degrees, such as, for example, 70 degrees. In the illustrative example shown in FIG. 1, the photoacoustic cell 18 may be generally conical in shape. However, it is contemplated that side walls 27 and 28 may intersect the front wall 32 and/or the back wall 30 at any suitable angles and, in some cases, at different relative angles, as desired. Further, it is contemplated that the front wall 32 and the back wall 30 need not be parallel to each other or even planar.

In some embodiments, at least one of the one or more walls 27, 28, 30 and 32 may act as the membrane to allow a gas to permeate through the wall and into the cavity 17. For example, at least one of the one or more walls 27, 28, 30, and 32 may include a membrane that a gas may permeate through. It is contemplated, however, that other suitable methods may be employed for providing a sample of gas into the photoacoustic cell 18, such as, for example, providing one or more holes for the gas to flow through.

In the illustrative embodiment of FIG. 1, an optical element 20 may define at least a portion of the front wall 32 of the photoacoustic cell 18. The optical element 20 may serve as an optical entrance to the photoacoustic cell 18, and may selectively transmit light beam 26 into the cavity 17. In some cases, the optical element 20 may include a material that is substantially transparent to at least some of the wavelength(s) of the electromagnetic radiation emanating from electromagnetic radiation source 12, which as described above, may correspond to an absorption line of a gas to be detected. In one embodiment, optical element 20 may include a band-pass filter configured to transmit a wavelength band that is within a certain range of the absorption line of the gas to be detected, or other desired range, as desired.

When interacting with an internal light beam 23 within the cavity 17, the optical element 20 may reflect the internal light beam 23 back into the cavity 17, particularly when the incident angle is at or greater than a threshold angle relative to a perpendicular line extending from the optical element 20, and may transmit internal light beam 23 out of the cavity 17 when the incident angle is less than the threshold angle. The threshold angle can vary depending on the index of the material of optical element 20, the band of wavelengths, the shape and/or orientation of the optical element, etc. By reflecting the internal light beam 23, the internal path length of the internal light beam 23 in the cavity 17 of photoacoustic cell 18 can be significantly increased. In some cases, the photoacoustic cell 18 may be configured to provide an incident angle greater than the threshold angle at least for the first hit of the internal light beam 23 with the back side (the side facing the cavity 17) of the optical element 20. Increasing the angle of incident and/or internal path length of the cavity 17 (relative to, for example, a cylindrical shaped cavity) may increase the acoustic intensity within the cavity 17 and sensor sensitivity.

In the illustrative embodiment, the detector 22 may be configured to detect the interaction (e.g. absorption) of the internal light beam 23 with the gas to be detected in the photoacoustic cell 18. In some cases, the detector 22 may be an acoustic detector, such as a microphone or other transducer that is configured to detect an acoustic signal such as one or more pressure pulses created by the absorption of the internal light beam 23 by the gas to be detected. In some cases, the detector 22 may produce a zero measurement when no gas is detected in the photoacoustic cell 18 (e.g. no gas is present that has an absorption line at or near the wavelength of the light source 12). In some cases, detector 22 can be mounted to an interior or an exterior of photoacoustic cell 18 such that the detector 22 is in acoustic communication with the gas sample. In some embodiments, detector 22 may be removably mounted to photoacoustic cell 18 by, for example, a clamp, but this is not required.

Although not required, a control module 24 can be provided to provide control and/or processing capabilities for the photoacoustic detection system 10. For example, control module 24 may be connected to detector 22 to receive one or more output signals corresponding to the interaction (e.g. absorption) of the internal light beam 23 with the gas sample. In some cases, the control module 24 can be configured to display information obtained from detector 22, and can be further configured to process such information. For example, control module 24 may be configured to determine the concentration of the gas to be detected in the gas sample, based on the output signal of the detector 22.

The control module 24 may also be connected to electromagnetic radiation source 12, and may modulate and/or pulse the electromagnetic radiation at a modulation frequency in order to produce a series of sound waves or photoacoustic signals in the cavity 17. It is contemplated that other methods or systems may be used to provide a desired modulation to the electromagnetic radiation source 12, as desired. With the modulated light beam 26, detector 22 may detect a modulated acoustic signal or pressure wave that, in some cases, may be at the same frequency that the modulated electromagnetic radiation. The amplitude of the detected acoustic signal may be used to determine a gas concentration.

In operation, the photoacoustic cell 18 may couple in light beam 26 through optical element (e.g. band-pass filter) 20 when, for example, the light beam 26 has a wavelength that corresponds to the absorption line of a gas to be detected. The light beam 26 may be modulated at a modulation frequency. Once in the cavity 17, the internal light beam 23 can be reflected around the cavity 17 and interact with the gas sample in the photoacoustic cell 18, generating an acoustic signal in the cavity 17 that is modulated at the modulating frequency of the modulated light beam 26. With the illustrative photoacoustic cell 18, at least a portion of the internal light beam 23 in the cavity 17 may be reflected off of the internal surface of the optical element 20 due to the incident angle (relative to, for example, a cylindrical cavity) being greater than a threshold angle. Detector 22 may detect the interaction (e.g. absorption) of the internal light beam 23 with the gas to be detected by detecting a pressure pulse or other acoustical signal whose magnitude is related to the amount of absorption of the electromagnetic radiation by the gas sample. Since the wavelength of the internal light beam 23 may be tuned by the electromagnetic radiation source 12 or otherwise correspond to an absorption line of a particular gas to be detected, the concentration of the particular gas in the gas sample can be determined by the amplitude of the detected modulated acoustical signal.

In some cases, and as shown in FIG. 1, the space between the electromagnetic radiation source 12 and the optical element 20 may be generally free from additional optical elements. As such, photoacoustic gas detection system 10 may be capable of increasing the internal path length of the internal light beam 23 by reflecting the internal light beam 23 off of the back side of the optical element 20 in the photoacoustic cell 18 (relative to, for example, a cylindrical shaped cavity) without requiring any additional optics between the electromagnetic radiation source 12 and the optical element 20. However, it is contemplated that in some embodiments, additional optical elements can be provided in this space, if desired.

Figure 2:
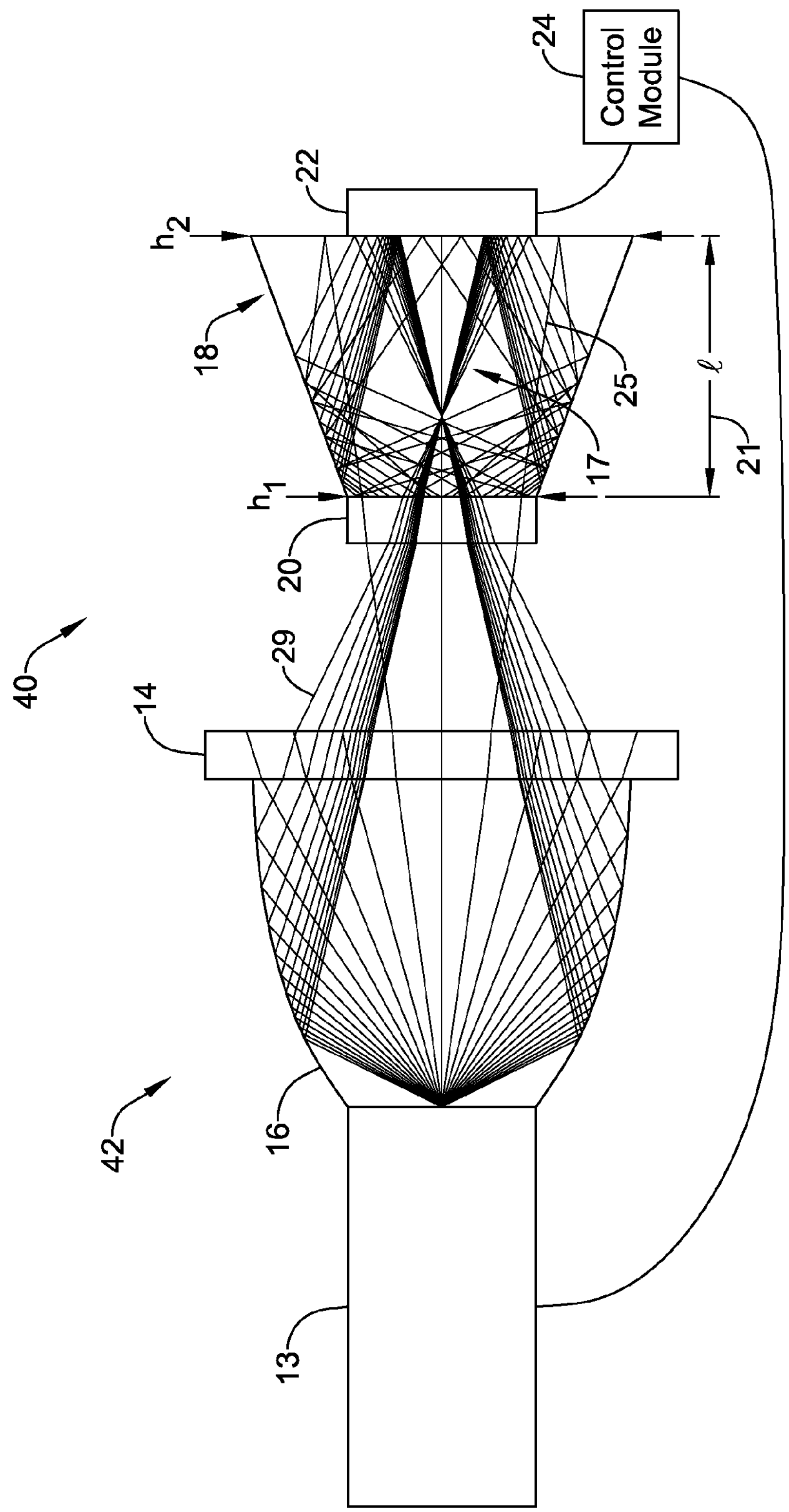
FIG. 2 is a schematic diagram of another illustrative photoacoustic gas detection system.

FIG. 2 is a schematic diagram of another illustrative photoacoustic gas detection system 40. As shown in FIG. 2, the light source 42 may include an illumination module 13, or lamp, for emitting a non-collimated light beam 29, collection optics 16 for collecting and, in some cases, re-directing the light beam 29, and an optical element 14. In the illustrative embodiment, most of the internal light beam 23 may be reflected off of optical element 20 at least once before leaking out of the cavity 17. In some embodiments, as shown in FIG. 2, the incoming light beam 29 may include a plurality of light rays that are focused to a focal point within cavity 17 of photoacoustic cell 18, but this is not required. In some cases, incoming light beam 29 may be focused to a focal point outside of the cavity of the photoacoustic cell 18.

In some embodiments, a space is provided between optical element 14 (e.g. a lens) of the light source 42 and optical element 20 (e.g. a band-pass filter), but this is not required. The space between the light source 42 and optical element 20 may, in some cases, help provide thermal isolation between the light source 42 and photoacoustic cell 18. Similar to that discussed above with reference to FIG. 1, the space between the light source 42 and the optical element 20 may be generally free from additional optical elements, but this is not required.

In the illustrative example of FIG. 2, the optical element 20 may be a band-pass filter, such as a 200 nanometer full width at half maximum intensity filter. However, this is just one example and is not meant to be limiting in any manner. It is contemplated that other band-pass filters may be used, depending on the application (e.g. depending on the wavelength of the gas to be detected). It is contemplated that the optical element 20 may also include other optical features. For example, the optical element 20 may be a lens, a diffraction grating, or any other suitable optical element, as desired.

In one illustrative example, the photoacoustic cell 18 may have back wall 30 spaced a distance of about 9.2 millimeter (mm) from the source of the light beam 29, such as lamp 13. In this example, an optical filter 14 may be spaced about 2 mm from the optical element 20, and the optical element 20 may be spaced about 2.75 mm from the back wall 30. Also, in the illustrative example, the optical element 20 and/or the front wall of the cavity 17 may have a height "$h_1$" of about 2 mm, and the back wall 30 of the cavity 17 may have a height "$h_2$" of about 4 mm. The length "l" 21 of the photoacoustic cell 18 may be, for example, 2.75 mm. These are just example dimensions that may be used for the photoacoustic detection system 40. Any other suitable dimensions may be used, as desired.

Figure 3:
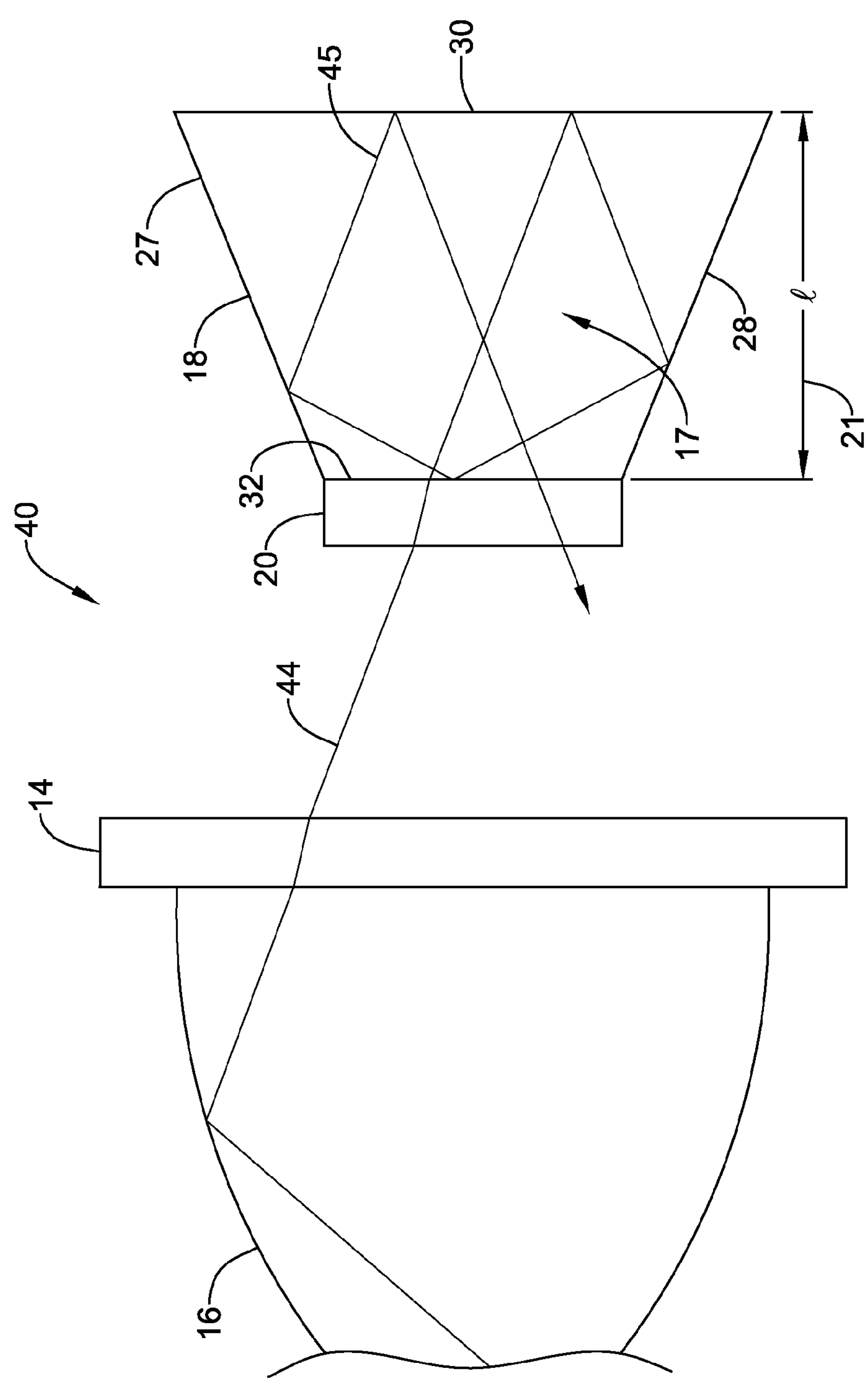
FIG. 3 is a schematic diagram showing the optical path of a single ray in the photoacoustic gas detection system shown in FIG. 2.

FIG. 3 is a partial schematic diagram showing the optical path of a single ray 44 in the photoacoustic gas detection system 40 shown in FIG. 2. As shown, ray 44 may enter the photoacoustic cavity 17 via optical element 20, and then the ray may first reflect off of back wall 30, then off side wall 28, and then reflect off the back side of front wall 32 or band-pass filter 14. As shown, because side wall 28 is at a non-orthogonal angle relative to the front wall 32, the incident angle of internal ray 45 at the front wall 32 may be sufficient to reflect internal ray 45 internally in cavity 17 (i.e. greater than threshold angle). After reflecting off of the front wall 32, internal ray 45 may reflect off of side wall 27, then off of back wall 30, and then may leak out of the cavity 17 through optical element 20, since the incident angle of ray may no longer be sufficient to cause internal reflection (i.e. less than the threshold angle). As can be seen, the incident angle of internal ray 45 for the first hit or interaction with the rear side of the front wall 32 is much greater than the incident angle of the internal ray 45 for the second hit or interaction. The at least one internal reflection of ray internal 45 off of optical element 20 may increase the total path length of internal ray 45 internal to cavity 17 of photoacoustic cell 18 (relative to, for example, a cylindrical cavity).

When the photoacoustic cell 18 is provided with the illustrative dimensions discussed above, the total path length in the photoacoustic cell 18 may be about 13 mm, which may be about double the total path length if there was no internal reflection off of the rear side of the optical element 20. Further, the total path length may be about 4.7 times the length "l" 21 of the photoacoustic cell 18. It is contemplated that the photoacoustic cavity 18 may be configured to provide an internal path length of about 3 times or more the length "l" 21 of the photoacoustic cell 18, about 4 times or more the length "l" 21 of the photoacoustic cell 18, about 5 times or more the length "l" 21 of the photoacoustic cell 18, about 6 times or more the length "l" 21 of the photoacoustic cell 18, about 7 times or more the length "l" 21 of the photoacoustic cell 18, or any other suitable multiplication of the length "l" 21 of the photoacoustic cell, as desired.

Further, while internal ray 45 is shown as being reflected off of the back side of the band-pass filter 20 only once, it is contemplated that the internal ray 45 may be reflected multiple times, depending on the shape of the photoacoustic cell 18 and the angle of incidence of the ray admitted to the photoacoustic cell 18.

Figure 4:
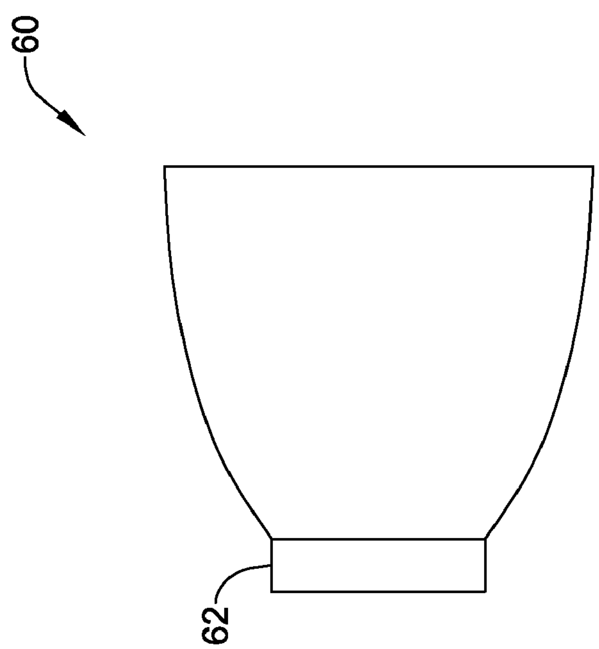
FIGS. 4-6 are schematic diagrams of other illustrative photoacoustic cells.
Figure 5:
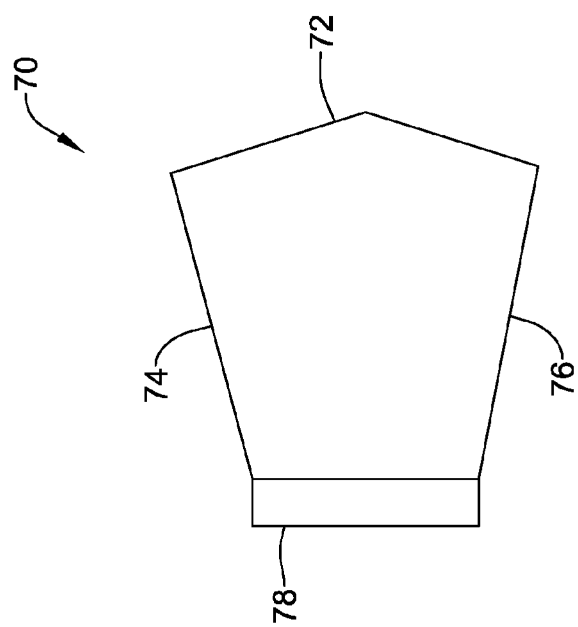
Figure 6:
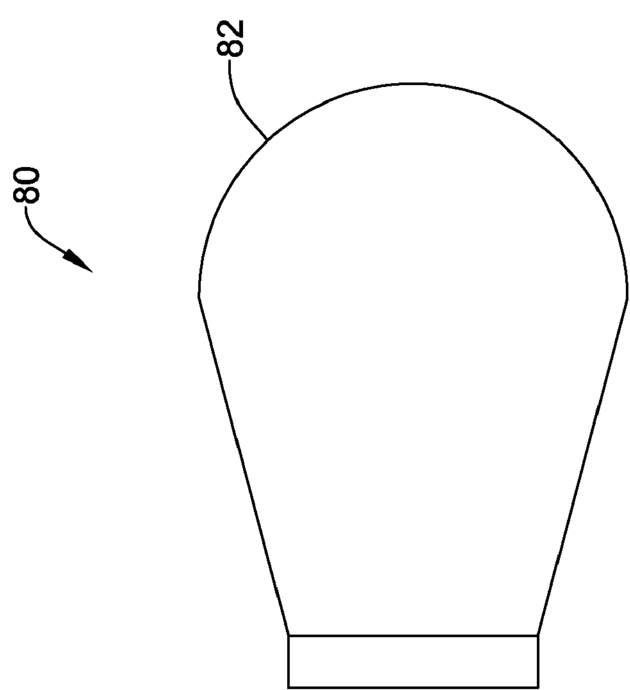

Additionally, it is contemplated that other shapes and/or configurations may be used to increase the total internal path length of the internal light beam for a given volume of the cavity 17 of photoacoustic cell 18. In many cases, the side walls, such as side walls 27 and 28, may be configured such that the cross-sectional area defined by the side walls increases from the front wall 32 toward the back wall 30. FIGS. 4-6 show other example photoacoustic cells that may be used to increase the total internal path length of an internal light beam for a given volume of the photoacoustic cavity. For example, as shown in FIG. 4, the photoacoustic cell 60 may be shaped similar to FIGS. 1-3, except the side walls may have a parabolic or other curved shape. Optical element 62, may be similar to optical element 20. Another example is shown in FIG. 5, which shows a photoacoustic cell 70 that includes a back wall 72 that is piecewise linear and not parallel to the back wall of optical element 78. The side walls 74 and 76 are similar to side walls 27 and 28 of FIGS. 1-3. Another example is shown in FIG. 6, which shows a photoacoustic cell 80 that includes a back wall 82 that is semi-hemispherical, parabolic, step-wise linear or any other suitable shape. The side walls are shown similar to side walls 27 and 28 of FIGS. 1-3. It is contemplated that the side walls may be curved, step-wise linear or any other shape. These are just a few examples. It is also contemplated that other protrusions and/or indentations or angles of walls may be used, as desired. It is also contemplated that other configurations and shaped of the photoacoustic cell may be used that increase the internal reflection relative to, for example, a cylindrical photoacoustic cell, as desired.

In some instances, the rear surface of the optical element 20, the side walls and/or the back wall of the photoacoustic cell may have a surface treatment that disperses the light rays in multiple directions. For example, the surfaces may include a micro pattern such as grooves, pillars or other shapes. This may help keep more of the light within the photoacoustic cell. In many cases, it is desirable to minimize the absorption of light by the internal walls of the photoacoustic cavity. This may be accomplished by appropriate material selection and design.

It is contemplated that any of the foregoing configurations or portions of the foregoing configurations may be mixed and matched, as desired.

Having thus described the preferred embodiments of the present invention, those of skill in the art will readily appreciate that yet other embodiments may be made and used within the scope of the claims hereto attached. It will be understood, however, that this disclosure is, in many respect, only illustrative. Changes may be made in details, particularly in matters of shape, size, and arrangement of parts without exceeding the scope of the invention. The invention's scope is, of course, defined in the language in which the appended claims are expressed.

What is claimed is:

1. A photoacoustic gas sensor comprising:

an electromagnetic radiation source configured to emit electromagnetic radiation;

a photoacoustic cell configured to receive a gas sample to be detected, wherein the photoacoustic cell includes an optical element adjacent the photoacoustic cell and configured to transmit at least part of the electromagnetic radiation into the photoacoustic cell, wherein the photoacoustic cell includes a front wall, a reflective back wall, and reflective side walls extending between the front wall and the back wall to collectively define an optical cavity, wherein the optical element is positioned adjacent the front wall and opposite the back wall, wherein the cross-sectional area defined by the side walls increases from the front wall toward the back wall, and wherein the electromagnetic radiation transmitted into the photoacoustic cell first reflects off the reflective back wall of the photoacoustic cell; and an acoustical detector acoustically coupled to the photoacoustic cell, the acoustical detector configured to detect an acoustic signal that is related to absorption of the electromagnetic radiation by the gas sample in the photoacoustic cell.

2. The photoacoustic gas sensor of claim 1, wherein the optical element is configured to only transmit a band of wavelengths corresponding to an absorption line of a gas to be detected.

3. The photoacoustic gas sensor of claim 1, wherein the electromagnetic radiation emitted by the electromagnetic radiation source has a wavelength corresponding to an absorption line of the gas to be detected.

4. The photoacoustic gas sensor of claim 1, wherein the optical cavity of the photoacoustic cell is shaped to increase an optical path length of the electromagnetic radiation internal to the photoacoustic cell.

5. The photoacoustic gas sensor of claim 1, wherein at least one of the side walls is at a non-orthogonal angle relative to the back wall.

6. The photoacoustic gas sensor of claim 1, wherein the back wall is non-parallel with the optical element.

7. The photoacoustic gas sensor of claim 1, wherein at least one of the back wall and side walls is curved.

8. The photoacoustic gas sensor of claim 1, wherein the photoacoustic cell is conical in shape.

9. The photoacoustic gas sensor of claim 1, wherein the photoacoustic gas sensor is generally free from optical elements positioned between the electromagnetic radiation source and the optical element of the photoacoustic cell.

10. A photoacoustic gas sensor comprising:

an electromagnetic radiation source configured to emit electromagnetic radiation;

a photoacoustic cell configured to receive a gas sample to be detected, wherein the photoacoustic cell includes an optical element adjacent the photoacoustic cell and configured to transmit at least part of the electromagnetic radiation into the photoacoustic cell, wherein the photoacoustic cell includes a front wall, a reflective back wall, and reflective side walls extending between the front wall and the back wall to collectively define an optical cavity, wherein the optical element is positioned adjacent the front wall and opposite the back wall, and wherein the cross-sectional area defined by the side walls increases from the front wall toward the back wall;

an acoustical detector acoustically coupled to the photoacoustic cell, the acoustical detector configured to detect an acoustic signal that is related to absorption of the electromagnetic radiation by the gas sample in the photoacoustic cell;

wherein the optical element includes a rear side facing toward the back wall of the photoacoustic cell;

wherein the rear side of the optical element reflects electromagnetic radiation when an incident angle of the electromagnetic radiation is greater than a threshold angle, and transmits electromagnetic radiation when the incident angle is less than the threshold angle; and wherein the photoacoustic cell is shaped such that at least a majority of the electromagnetic radiation that is transmitted through the optical element and into the cavity of the photoacoustic cell has an incident angle that is greater than the threshold angle for at least a first time that the electromagnetic radiation returns to the rear side of the optical element.

11. A photoacoustic gas sensor comprising:

an electromagnetic radiation source configured to emit electromagnetic radiation;

a photoacoustic cell configured to receive a gas sample to be detected, wherein the photoacoustic cell includes an optical element adjacent the photoacoustic cell that is configured to transmit at least part of the electromagnetic radiation into the photoacoustic cell, wherein the photoacoustic cell includes a front wall, a reflective back wall, and reflective side walls extending between the front wall and the back wall to collectively define an optical cavity, wherein the optical element is positioned adjacent to and/or forms at least part of the front wall, and wherein the cross-sectional area defined by the side walls increases monotonically from the front wall toward the back wall; and an acoustical detector acoustically coupled to the photoacoustic cell, the acoustical detector configured to detect an acoustic signal that is related to absorption of the electromagnetic radiation by the gas sample in the photoacoustic cell.

12. The photoacoustic gas sensor of claim 11, wherein at least one of the side walls is at a non-orthogonal angle relative to the back wall.

13. The photoacoustic gas sensor of claim 11, wherein at least one of the back wall and side walls is curved.

* * * * *